United States Patent

Lantzsch et al.

[11] Patent Number: 5,874,586
[45] Date of Patent: Feb. 23, 1999

[54] PROCESS FOR PREPARING 1-ARYL-4-CARBAMOYL-TETRAZOLINONES

[75] Inventors: Reinhard Lantzsch, Wuppertal; Uwe Stelzer, Burscheid; Carl Casser, Köln, all of Germany

[73] Assignee: Bayer Aktiengesellschaft, Leverkusen, Germany

[21] Appl. No.: 18,484

[22] Filed: Feb. 4, 1998

Related U.S. Application Data

[63] Continuation-in-part of Ser. No. 715,291, Sep. 16, 1996, abandoned.

[30] Foreign Application Priority Data

Sep. 22, 1995 [DE] Germany .................. 195 35 242.4

[51] Int. Cl.$^6$ .................. C07D 257/04; C07D 401/06; C07D 403/06
[52] U.S. Cl. .................. 548/251; 546/210; 540/603
[58] Field of Search .................. 548/251; 546/210; 540/603

[56] References Cited

U.S. PATENT DOCUMENTS

| | | |
|---|---|---|
| 4,044,018 | 8/1977 | Tomita et al. . |
| 4,830,661 | 5/1989 | Covey et al. . |
| 5,686,392 | 11/1997 | Stelzer et al. . |

FOREIGN PATENT DOCUMENTS

| | | |
|---|---|---|
| 0 146 279 A1 | 6/1985 | European Pat. Off. . |
| 0 202 929 A3 | 11/1986 | European Pat. Off. . |
| 0 572 855 A1 | 12/1993 | European Pat. Off. . |
| 0 578 090 A2 | 1/1994 | European Pat. Off. . |
| 0 612 735 A1 | 8/1994 | European Pat. Off. . |
| 0 646 577 A1 | 4/1995 | European Pat. Off. . |

OTHER PUBLICATIONS

O. Tsuge et al, J.Org.Chem., vol. 45, pp. 5130–5136 (1980).
Chemical Abstracts, 1994, vol. 80, abstract No. 82829r, p. 391, English language abstract of Z.Chem. 1973, 13(11) pp. 429–30 (above Reference AL).
J. Horwitz et al, J.Am.Chem.Soc., vol. 81, pp. 8076–3079 (1959).

*Primary Examiner*—Patricia L. Morris
*Attorney, Agent, or Firm*—Sprung Kramer Schaefer & Briscoe

[57] ABSTRACT

Herbicidally active 1-aryl-4-carbamoyl-tetrazolinones of the formula (I)

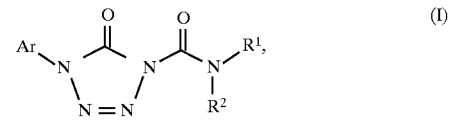

in which

Ar represents optionally substituted aryl, $R^1$ represents in each case optionally substituted alkyl, alkenyl, alkinyl or alkoxy, and $R^2$ represents in each case optionally substituted alkyl, alkenyl, alkinyl, cycloalkyl, cycloalkylalkyl, aryl or arylalkyl, or, together with $R^1$, represents alkanediyl, are obtained in good yields and at high purity by reacting 1-aryl-tetrazolinones of the formula (II) with phosgene in the presence of a diluent at temperatures of between 0° C. and 150° C. ("first process step"), and reacting the resulting (novel) 1-aryl-4-chlorocarbonyl-tetrazolinones of the formula (III) with amines of the formula (IV) in the presence of a diluent, and, where appropriate, in the presence of a further basic compound, at temperatures of between −20° C. and +100° C. ("second process step"):

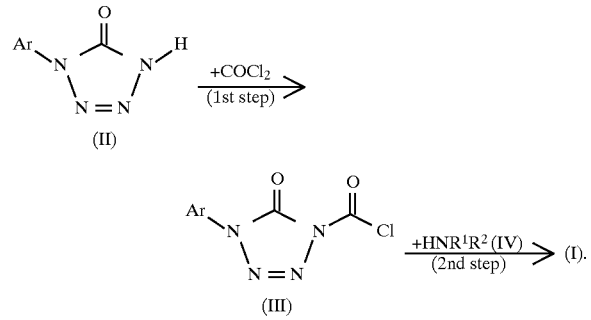

3 Claims, No Drawings

PROCESS FOR PREPARING 1-ARYL-4-CARBAMOYL-TETRAZOLINONES

This is a continuation-in-part of U.S. application Ser. No. 08/715,291, filed Sep. 16, 1996 (now abandoned).

The invention relates to a novel process and novel intermediates for preparing 1-aryl-4-carbamoyl-tetrazolinones which are known to be herbicidally active compounds.

It has been disclosed that substituted carbamoyltetrazolinones are obtained when corresponding tetrazolinones are reacted with suitable carbamic acid derivatives (cf. EP-A 146279, EP-A 202929, EP-A 578090 and EP-A 612735). In this manner of preparation, an (undesirable) O-carbamoylation is also always observed in addition to the desired N-carbamoylation (with regard to the acylation of tetrazolinones, cf. Z. Chemie 13 (1973), 429–430, as well). Consequently, products which are more or less heavily contaminated are obtained in many cases.

It has furthermore been disclosed that 1-alkyl-4-chlorocarbonyl-tetrazolinones are obtained when 1-alkyl-tetrazolinones are reacted with phosgene in the presence of a tertiary amine (cf. U.S. Pat. No. 4,830,661). However 1-aryl-4-chlorocarbonyl-tetrazolinones have still not been disclosed in the literature and cannot be obtained, either, in useful yield and quality by means of the known process.

It has now been found that 1-aryl-4-carbamoyl-tetrazolinones of the general formula (I)

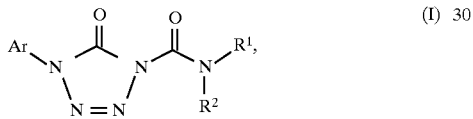

in which
Ar represents optionally substituted aryl,
$R^1$ represents in each case optionally substituted alkyl, alkenyl, alkinyl or alkoxy, and
$R^2$ represents in each case optionally substituted alkyl, alkenyl, alkinyl, cycloalkyl, cycloalkylalkyl, aryl or arylalkyl
or, together with $R^1$, represents alkanediyl,
are obtained in very good yields and at high purity when 1-aryl-tetrazolinones of the general formula (II)

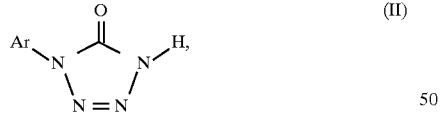

in which
Ar has the abovementioned meaning,
are reacted with phosgene in the presence of a diluent at temperatures of between 0° C. and 150° C. ("first process step") and the resulting 1-aryl-4-chlorocarbonyltetrazolinones of the general formula (III)

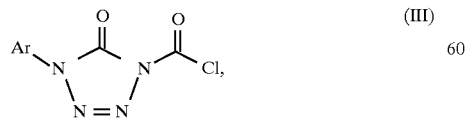

in which
Ar has the abovementioned meaning,
—where appropriate after intermediate isolation or without intermediate isolation— are reacted with amines of the general formula (IV)

in which
$R^1$ and $R^2$ have the above mentioned meaning,
in the presence of a diluent and, where appropriate, in the presence of further basic compound at temperatures of between −20° C. and +100° C. ("second process step").

Surprisingly, 1-aryl-4-carbamoyl-tetrazolinones of the general formula (I) can be prepared in a simpler, economically more favorable manner, and also in higher yields and in better quality, by the process according to the invention than by the known methods.

The process according to the invention consequently constitutes a valuable enrichment of the state of the art.

The process according to the invention preferably relates to the preparation of compounds of the formula (I) in which
Ar represents phenyl or naphthyl which are optionally substituted by carboxyl, cyano, carbamoyl, nitro, amino, hydroxyl or halogen, or by $C_1$–$C_4$-alkyl, $C_1$–$C_4$-alkoxy, $C_1$–$C_4$-alkylthio, $C_1$–$C_4$-alkylsulfinyl, $C_1$–$C_4$-alkylsulfonyl, di-($C_1$–$C_4$-alkyl)amino, $C_1$–$C_4$-alkylsulfonylamino, di-($C_1$–$C_4$-alkyl)aminosulfonyl, $C_1$–$C_4$-alkyl-carbonyl, $C_1$–$C_4$-alkyl-carbonylamino, $C_1$–$C_4$-alkoxycarbonyl, di-($C_1$–$C_4$-alkylamino)-carbonyl, $C_1$–$C_4$-alkylenedioxy, phenyl or phenoxy (which are in each case optionally substituted by fluorine and/or chlorine),
$R^1$ represents alkyl, alkenyl or alkinyl which in each case have 1 to 6 carbon atoms and which are in each case optionally substituted by cyano or halogen, and
$R^2$ represents alkyl which has 1 to 6 carbon atoms and which is optionally substituted by cyano or halogen, represents alkenyl or alkinyl which have in each case 2 to 6 carbon atoms and which are in each case optionally substituted by cyano or halogen, represents cycloalkyl or cycloalkylalkyl which have in each case 3 to 6 carbon atoms in the cycloalkyl moiety and optionally 1 to 2 carbon atoms in the alkyl moiety and which are in each case optionally substituted by cyano, halogen or $C_1$–$C_4$-alkyl, or represents phenyl or phenyl-$C_1$–$C_2$-alkyl which are in each case optionally substituted by cyano, nitro or halogen, or by $C_1$–$C_4$-alkyl, $C_1$–$C_4$-alkoxy, $C_1$–$C_4$-alkylthio, $C_1$–$C_4$-alkylsulfinyl, $C_1$–$C_4$-alkylsulfonyl, di-($C_1$–$C_4$-alkyl)amino, $C_1$–$C_4$-alkylsulfonylamino, di-($C_1$–$C_4$-alkyl)aminosulfonyl, $C_1$–$C_4$-alkyl-carbonyl or $C_1$–$C_4$-alkoxy-carbonyl (which are in each case optionally substituted by fluorine and/or chlorine),
or, together with $R^1$, represents alkanediyl having 2 to 6 carbon atoms.

The process according to the invention relates, in particular, to the preparation of compounds of the formula (I) in which
Ar represents phenyl which is optionally substituted by cyano, fluorine, chlorine or bromine, or by methyl, ethyl, n- or i-propyl, methoxy, ethoxy, n- or i-propoxy, methylthio, ethylthio, n- or i-propylthio, methylsulfinyl, ethylsufinyl, methylsulfonyl, ethylsulfonyl, dimethylaminosulfonyl, diethylaminosulfonyl, methylcarbonyl, ethylcarbonyl, n- or i-propylcarbonyl, methoxycarbonyl, ethoxycarbonyl, n- or i-propoxycarbonyl, dimethylaminocarbonyl, diethylaminocarbonyl, methylenedioxy or ethylenedioxy (which are in each case optionally substituted by fluorine and/or chlorine), R¹ represents methyl, ethyl, n- or i-propyl, n-, i- or s-butyl, propenyl, butenyl, propinyl or butinyl which are in each case optionally substituted by cyano, fluorine or chlorine, and R² represents methyl, ethyl, n- or i-propyl, n-, i- or s-butyl, propenyl, butenyl, propinyl or butinyl which are in each case optionally substituted by cyano, fluorine or chlorine, represents cyclopropyl, cyclobutyl, cyclopentyl, cyclohexyl, cyclopropylmethyl, cyclobutylmethyl, cyclopentylmethyl or cyclohexylmethyl which are in each case optionally substituted by cyano, fluorine, chlorine, bromine, methyl or ethyl, or represents phenyl, benzyl or phenylethyl which are in each case optionally substituted by cyano, fluorine, chlorine, methyl, ethyl, methoxy or ethoxy, or, together with R¹, represents butane-1,4-diyl (tetramethylene) or pentane-1,5-diyl (pentamethylene).

The above listed general radical definitions, or those listed in preference ranges, apply both to the end products of the formula (I) and also, correspondingly, to the starting compounds or intermediates which are in each case required for the preparation. These radical definitions may be combined arbitrarily among each other, that is also between the given preferred ranges.

If, for example, 1-(2-fluoro-phenyl)-1,4-dihydro-5H-tetrazol-5-one and phosgene are used as starting compounds in the first step, and diethylamine is used as the starting compound in the second step, the course of the reaction in the process according to the invention can then be outlined by the following formula scheme:

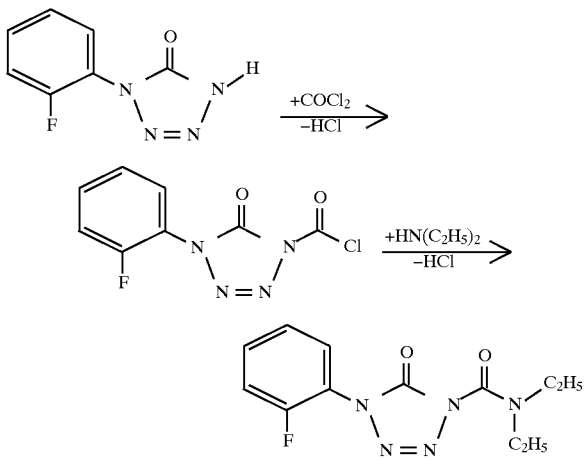

The 1-aryl-tetrazolinones which are to be used as starting compounds in the process according to the invention for preparing the compounds of formula (I) are defined generally by the formula (II). In the formula (II), Ar preferably or in particular has that meaning which has already been given above, in the description of the compounds of the formula (I) which are to be prepared in accordance with the invention, as being preferred or as being particularly preferred for Ar.

The starting compounds of the formula (II) are known and/or can be prepared by processes which are known per se (cf. J. Am. Chem. Soc. 81 (1959), 3076–3079; J. Org. Chem. 45 (1980), 5130–5136; EP-A 146279; EP-A 572855; EP-A 578090).

The 1-aryl-4-chlorocarbonyl-tetrazolinones which are formed in the first step of the process according to the invention for preparing the compounds of the formula (I) are defined generally by the formula (III). In the formula (III), Ar preferably or in particular has that meaning which has already been given above, in the description of the compounds of the formula (I) which are to be prepared in accordance with the invention, as being preferred or as being particularly preferred for Ar.

The 1-aryl-4-chlorocarbonyl-tetrazolinones of the general formula (III) has still not been disclosed in the literature; as novel compounds, they are also the subject-matter of the present application.

The amines which—in the second step—are also to be used as starting compounds in the process according to the invention for preparing the compounds of the formula (I) are defined generally by the formula (IV). In the formula (IV), R¹ and R² preferably or in particular have that meaning which has already been given above, in the description of the compounds of the formula (I) which are to be prepared in accordance with the invention, as being preferred or as being particularly preferred for R¹ and R².

The starting compounds of the formula (IV) are known synthesis chemicals.

The process according to the invention for preparing the compounds of the formula (I) is carried out in the presence of a diluent. Organic solvents which are inert toward phosgene preferably come into consideration as diluents for the first step. These solvents include, in particular, aliphatic, alicyclic and aromatic, optionally halogenated hydrocarbons, for example pentane, hexane, heptane, petroleum ether, ligroin, benzine, benzene, toluene, xylene, chlorobenzene, dichlorobenzene, cyclohexane, methylcyclohexane, dichloromethane (methylene chloride), trichloromethane (chloroform) or tetrachloromethane, dialkyl ethers, for example diethyl ether, diisopropyl ether, methyl t-butyl ether (MTBE), ethyl t-butyl ether, methyl t-pentyl ether (TAME), ethyl t-pentyl ether, tetrahydrofuran (THF), 1,4-dioxane, ethylene glycol dimethyl ether, ethylene glycol diethyl ether, diethylene glycol dimethyl ether or diethylene glycol diethyl ether; dialkyl ketones, for example acetone, butanone (methyl ethyl ketone), methyl i-propyl ketone or methyl i-butyl ketone; nitrites, for example acetonitrile, propionitrile, butyronitrile or benzonitrile; esters, for example methyl acetate, ethyl acetate, n- or i-propyl acetate, or n-, i- or s-butyl acetate; sulfoxides, for example dimethyl sulfoxide.

Toluene, xylene, dichloroethane and chlorobenzene may be mentioned as diluents which are particularly preferred for the first step.

Essentially the same diluents can be used for the second process step as those used when carrying out the first process step. Tetrahydrofuran and chlorobenzene (the latter in particular when implementing a "one-pot process") are to be mentioned as being particularly preferred diluents.

The process according to the invention for preparing the compounds of the formula () is optionally carried out, in the second step, in the presence of an additional basic compound—in addition to the amine of the formula (IV). In general the customary inorganic or organic bases or acid acceptors come into consideration as basic compounds. These basic compounds preferably include alkali metal or alkaline earth metal acetates, amides, carbonates, hydrogen carbonates, hydrides, hydroxides or alkoxides, for example sodium, potassium or calcium acetate, lithium, sodium, potassium or calcium amide, sodium, potassium or calcium carbonate, sodium, potassium or calcium hydrogen carbonate, lithium, sodium, potassium or calcium hydride, lithium, sodium, potassium or calcium hydroxide, or sodium or potassium methoxide, ethoxide, n- or i-propoxide, or n-, i-, s- or t-butoxide; furthermore, also basic organic nitrogen compounds, for example trimethylamine, triethylamine, tripropylamine, tributylamine, ethyldiisopropylamine, N,N-dimethyl-cyclohexylamine, dicyclohexylamine, ethyldicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2.2.2]-octane (DABCO), 1,5-diazabicyclo-[4.3.0]-non-5-ene (DBN) and 1,8-diazabicyclo[5.4.0]-undec-7-ene (DBU).

In a preferred embodiment of the process according to the invention, the amine of the formula (IV) is employed in an appropriate excess, and is consequently used as the base, and no use is made of an additional basic compound.

The reaction temperatures may be varied over a relatively wide range while carrying out the process according to the invention. In general, temperatures of between 0° C. and 150° C., preferably of between 50° C. and 120° C., are employed in the first step while temperatures of between −20° C. and +100° C., preferably of between 0° C. and 80° C., are employed in the second step.

In general, the process according to the invention is carried out under atmospheric pressure in both steps. However, it is also possible to carry out the process according to the invention under increased or reduced pressure—in general between 0.1 bar and 10 bar.

In general, in order to carry out the process according to the invention, between 1 and 10 mol, preferably between 2 and 5 mol, of phosgene (first step) and between 1 and 4 mol, preferably between 2 and 3 mol, of amine of the formula (IV) (second step) are employed per mole of starting compound of the formula (II).

In a preferred embodiment of the first step of the process according to the invention, the phosgene is initially introduced in a diluent and the 4-aryl-tetrazolinone of the formula (II) is slowly added to it. The reaction mixture is then—preferably while passing in phosgene—heated to the reaction temperature which is required in each case and—preferably while continuing to pass in phosgene—kept at this temperature until the conversion into the compounds of the formula (III) has finished. Excess phosgene is then largely removed—preferably by passing in nitrogen. The intermediate of the formula (III) can be isolated by carefully is distilling off the diluent under reduced pressure.

In a further preferred embodiment of the process according to the invention ("one-pot process"), the intermediate of the formula (III) is not isolated and an amine of the formula (IV) is added directly to the reaction solution which is present after carrying out the first step (after removing the excess phosgene). The mixture is then stirred until the reaction has finished, and is worked up using customary methods. For example, washing with water takes place—where appropriate after concentrating and taking up in an organic solvent which is practically immiscible with water, for example methylene chloride,—and this is followed by drying, filtering and concentrating carefully under reduced pressure, with the product of the formula (I) remaining as the residue.

The 1-aryl-4-carbamoyl-tetrazolinones of the formula (1) which can be prepared in accordance with the invention can be used as herbicides for controlling undesirable plant growth (cf. EP-A 146279, EP-A 202929, EP-A 578090 and EP-A 612735).

PREPARATION EXAMPLES

Example 1

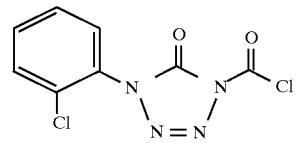

(1st Step)

4.9 g (25 mmol) of 1-(2-chloro-phenyl)-1,4-dihydro-5H-tetrazol-5-one are introduced in portions into a solution of 7.4 g (75 mmol) of phosgene in 50 ml of toluene. The mixture is heated to 60° C. while continuing to pass in phosgene. The reaction mixture is then, within the space of approximately 3 hours and while continuing to pass in phosgene gently, brought to reflux temperature, with phosgene then continuing to be passed in for a further 60 minutes approximately. The excess phosgene is subsequently blown off with nitrogen and the remaining solution is carefully concentrated under a water suction vacuum.

6.4 g (99% of theory) of 1-(2-chloro-phenyl)-4-chlorocarbonyl-1,4-dihydro-5H-tetrazol-5-one are obtained as a white crystalline residue with a melting point of 188° C. (with decomposition).

The IR spectrum of the product exhibits an absorption at 1810 cm$^{-1}$ which is characteristic for carbonyl groups.

Example 2

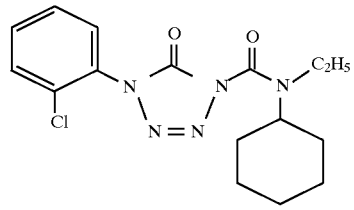

(2nd Step)

6.4 g (25 mmol) of 1-(2-chloro-phenyl)-4-chlorocarbonyl-1,4-dihydro-5H-tetrazol-5-one are dissolved in 50 ml of tetrahydrofuran, and a solution of 6.9 g (54 mmol) of N-ethyl-cyclohexylamine in 30 ml of tetrahydrofuran is added to it dropwise while stirring. The reaction mixture is stirred at approximately 20° C. for 2 hours and is then concentrated under a water suction vacuum. The residue is taken up in methylene chloride, and this solution is washed three times with water, dried with sodium sulfate and filtered. The solvent is carefully distilled off from the filtrate under a water suction vacuum.

7.9 g (91% of theory) of 1-(2-chloro-phenyl)-4-(N-cyclohexyl-N-ethylaminocarbonyl)-1,4-dihydro-5H-tetrazol-5-one are obtained as a white crystalline residue with a melting point of 78° C.

Example 3

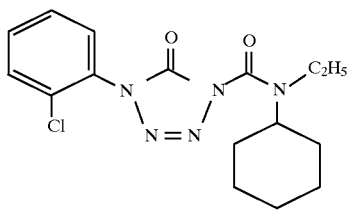

(1st+2nd Steps)

9.9 g of phosgene (100 mmol) are initially introduced in 200 ml of chlorobenzene, and 9.8 g (50 mmol) of 1-(2-chloro-phenyl)-1,4-dihyro-5H-tetrazol-5-one are added to it in portions. The mixture is stirred at approximately 20° C. for one hour and is then slowly heated, while continuing to pass in phosgene, to approximately 100° C., resulting in a clear solution being formed. Phosgene continues to be passed in for a further hour and the mixture is then stirred at approximately 100° C. for a further hour. Excess phosgene and hydrogen chloride are blown off with nitrogen. Then, after the reaction mixture has been cooled down to approximately 20° C., a solution of 12.7 g (100 mmol) of N-ethyl-cyclohexylamine in 30 ml of chlorobenzene is added to it dropwise while stirring, and the stirring is continued for another hour approximately. The mixture is then washed three times with water, dried with sodium sulfate and filtered. The solvent is carefully distilled off from the filtrate under a water suction vacuum.

15.9 g (91% of theory over both steps) of 1-(2-chloro-phenyl)-4-(N-cyclohexyl-N-ethylaminocarbonyl)-1,4-dihydro-5H-tetrazol-5-one are obtained as a white crystalline residue with a melting point of 77° C.

Comparative Example (Analogous to U.S. Pat. No. 4,830,661, Example 1)

A 23.3% solution of phosgene in toluene (85 g, 0.2 mol) is diluted with 100 ml of toluene and cooled down to 10° C. A solution of 41.4 g (0.16 mol) of 1-(2-chloro-phenyl)-1,4-dihydro-5H-tetrazol-5-one, 17 g (0.168 mol) of triethylamine and 0.2 g (1.6 mmol) of 4-dimethylaminopyridine in 70 ml of toluene is added to it dropwise within the space of approximately 10 minutes, with the temperature of the reaction mixture being kept below 28° C. The mixture is stirred at approximately 20° C. for approximately 30 minutes and is then filtered. The filtrate is concentrated under a water suction vacuum and the residue is taken up in methylene chloride; this solution is washed three times with water, dried with sodium sulfate and filtered. The solvent is carefully distilled off from the filtrate under a water suction vacuum.

The crude 1-(2-chloro-phenyl)-4-chlorocarbonyl-1,4-dihydro-5H-tetrazol-5-one, thereby obtained, is added portionwise to a solution of 38.0 g (0.3 mol) of N-ethyl-cyclohexylamine in 300 ml of dry methylene chloride, while stirring and cooling (exothermic reaction). The reaction mixture (a beige-colored suspension) is stirred for further 8 hours at room temperature, then washed three times with water, dried with sodium sulfate and filtered. The solvent is carefully distilled off from the filtrate under a water suction vacuum. The viscous-oily residue (which could not be crystallized, either with toluene/hexane or with other solvents) is dried in vacuo at 60° C.

45.7 g are obtained of a dark, viscous oil which has the following composition:

44.2% of 1-(2-chloro-phenyl)-4-(N-cyclohexyl-N-ethylaminocarbonyl)-1,4-dihydro-5H-tetrazol-5-one 44.2% of 1-(2-chloro-phenyl)-1,4-dihydro-5H-tetrazol-5-one, and 8% of 1 -(2-chloro-phenyl)-3 -cyclohexyl-3 -ethyl-urea.

It will be appreciated that the instant specification and claims are set forth by way of illustration and not limitation, and that various modifications and changes may be made without departing from the spirit and scope of the present invention.

We claim:

1. A process for preparing a 1-aryl-4-carbamoyltetrazolinone of formula I:

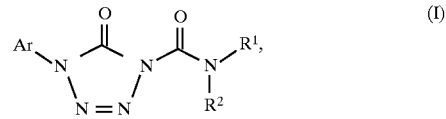

in which

Ar represents phenyl or naphthyl which-are optionally substituted by carboxyl, cyano, carbamoyl, nitro, amino, hydroxyl or halogen, or by $C_1$–$C_4$-alkyl, $C_1$–$C_4$-alkoxy, $C_1$–$C_4$-alkylthio, $C_1$–$C_4$-alkylsulfinyl, $C_1$–$C_4$-alkylsulfonyl, di-($C_1$–$C_4$-alkyl)amino, $C_1$–$C_4$-alkylsulfonylamino, di-($C_1$–$C_4$-alkyl)aminosulfonyl, $C_1$–$C_4$-alkyl-carbonyl, $C_1$–$C_4$-alkyl-carbonylamino, $C_1$–$C_4$ -alkoxy-carbonyl, di-($C_1$–$C_4$-alkylamino)-carbonyl, $C_1$–$C_4$-alkylenedioxy, phenyl or phenoxy which are in each case optionally substituted by fluorine or chlorine, $R^1$ represents alkyl, alkenyl or alkinyl which in each case have 1 to 6 carbon atoms and which are in each case optionally substituted by cyano or halogen, and $R^2$ represents alkyl which has 1 to 6 carbon atoms and which is optionally substituted by cyano or halogen, represents alkenyl or alkinyl which have in each case 2 to 6 carbon atoms and which are in each case optionally substituted by cyano or halogen, represents cycloalkyl or cycloalkylalkyl which have in each case 3 to 6 carbon atoms in the cycloalkyl moiety and optionally 1 to 2 carbon atoms in the alkyl moiety and which are in each case optionally substituted by cyano, halogen or $C_1$–$C_4$-alkyl, or represents phenyl or phenyl-$C_1$–$C_2$-alkyl which are in each case optionally substituted by cyano, nitro or halogen, or by $C_1$–$C_4$-alkyl, $C_1$–$C_4$-alkoxy, $C_1$–$C_4$-alkylthio, $C_1$–$C_4$-alkylsulfinyl, $C_1$–$C_4$-alkylsulfonyl, di-($C_1$–$C_4$-alkyl)amino, $C_1$–$C_4$-alkylsulfonylamino, di-($C_1$–$C_4$-alkyl)aminosulfonyl, $C_1$–$C_4$-alkyl-carbonyl or $C_1$–$C_4$-alkoxycarbonyl which are in each case optionally substituted by fluorine or chlorine, or, together with $R^1$, represents alkanediyl having 2 to 6 carbon atoms wherein a 1-aryl-tetrazolinone of the formula (II)

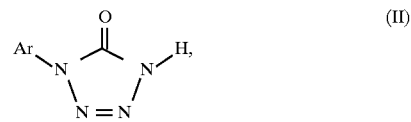

in which

Ar has the abovementioned meaning, is reacted with phosgene in the presence of a diluent at temperatures of between 0° C. and 150° C. in the absence of an auxiliary base and catalyst as a first process step and the resulting 1-aryl-4-chlorocarbonyl-tetrazolinone of the formula (III)

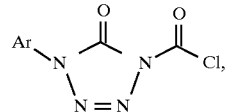  (III)

in which

Ar has the abovementioned meaning, with or without intermediate isolation is reacted with an amine of the general formula (IV)

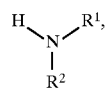  (IV)

in which $R^1$ and $R^2$ have the above mentioned meaning, in the presence of a diluent and, optionally, in the presence of a further basic compound at temperatures of between −20° C. and +100° C. as a second process step.

2. The process according to claim 1, wherein the first process step is carried out at temperatures of between 50° C. and 120° C.

3. The process according to claim 1, wherein the second process step is carried out at temperatures of between 0°C. and 80° C.

* * * * *